United States Patent [19]

Weber

[11] 4,006,056

[45] Feb. 1, 1977

[54] CONTROLLED RELEASE COMPOSITION CONTAINING STABILIZED UREASE

[75] Inventor: Meyer Michael Weber, Milwaukee, Wis.

[73] Assignee: Midwest Biochemical Corporation, Milwaukee, Wis.

[22] Filed: Sept. 19, 1975

[21] Appl. No.: 614,920

[52] U.S. Cl. .................................... 195/2; 21/55;
195/63; 195/68; 424/72
[51] Int. Cl.² ........................................ C12B 1/00
[58] Field of Search ........... 195/63, 68, 2, DIG. 11;
210/2, 11; 424/93, 76, 94; 4/109; 239/60;
252/134, 174, DIG. 12, DIG. 16; 21/55;
134/22 C, 42

[56] References Cited

UNITED STATES PATENTS

| | | | |
|---|---|---|---|
| 1,408,535 | 3/1922 | Ressler | 424/76 |
| 1,679,250 | 7/1928 | Lind | 195/68 |
| 3,798,128 | 3/1974 | Minato et al. | 252/DIG. 12 |
| 3,798,181 | 3/1974 | Vazquez | 252/174 |
| 3,824,633 | 7/1974 | Van Vlahakis | 4/109 |

*Primary Examiner*—R. B. Penland
*Attorney, Agent, or Firm*—Andrus, Sceales, Starke & Sawall

[57] ABSTRACT

This invention relates to a solid isotropic composition comprising a controlled release agent and stabilized urease. This composition is particularly suited for digestively reacting with various coatings on urinal discharge systems which coatings are subjected to a flow of water ranging from constant to intermittent.

14 Claims, 2 Drawing Figures

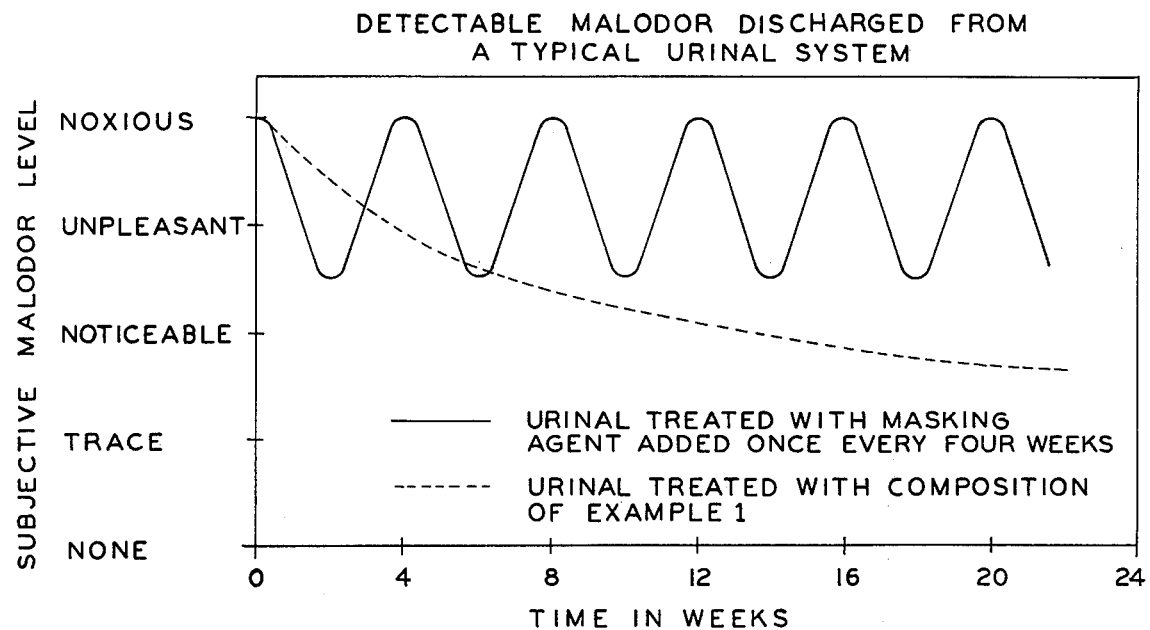
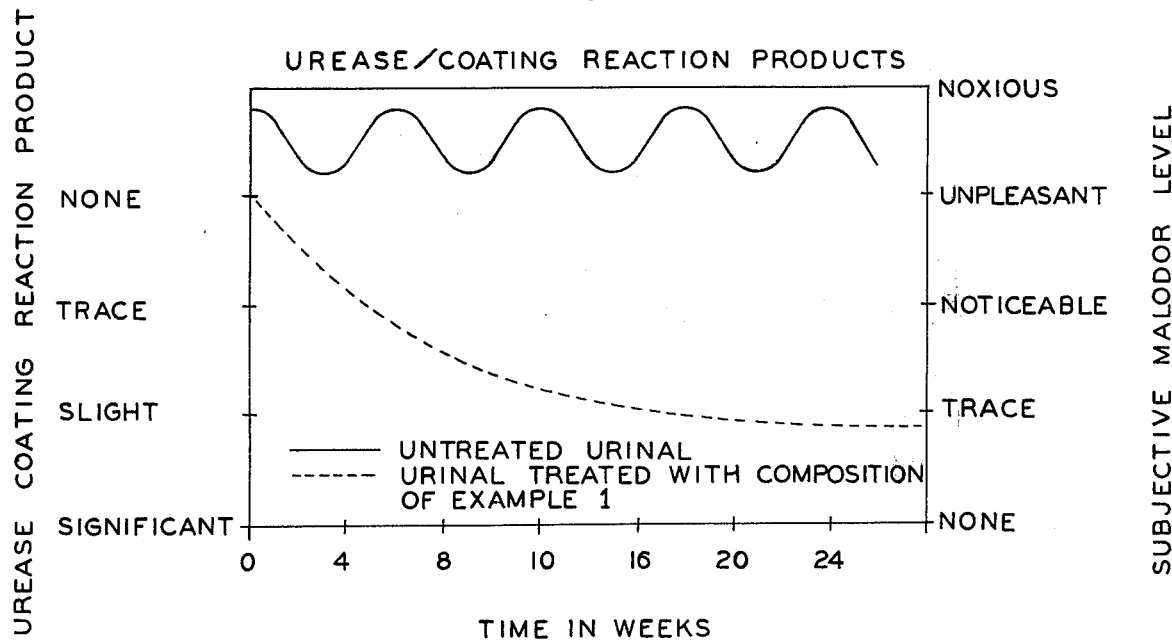

CONTROLLED RELEASE COMPOSITION CONTAINING STABILIZED UREASE

BACKGROUND OF THE INVENTION

This invention relates to a composition of matter suitable for treating the odor problem characteristic of public urinals. Over the years it has been found that urinals generally used in public rest rooms such as in railroads, bus terminals, restaurants, theaters, schools and public office buildings develop continuous pungent malodors. This odor problem heretofore has been generally treated by employing various types of odor masking agents, ranging from various odor blocks which are placed in urinals to the use of deodorants which are discharged into the air of the rest room from various types of intermittent or continuous air sanitizing, air freshner discharge devices. These masking agents have generally gained a reputation of producing a cheap odor now identified with public rest rooms and considered by many to be, at best, a poor improvement over the odor problem they were designed to alleviate. The masking approach to this odor problem is now generally recognized as a poor solution, and of course, is limited to only alleviating the odor while doing little to arrest or control the source of the odor.

SUMMARY OF THE INVENTION

The invention relates to the control of odor in a urinal by flushing the insoluble urinal coating with a solid isotropic composition containing a controlled release agent and stabilized urease.

An object of the present invention is to provide a composition of matter and method for treating the malodors common to public rest rooms and the like.

A further object of the invention is to provide a composition of matter suitable for modifying organometallo coatings on various substrates wherein the coatings contain the organo moiety $[N(R)_x]_y$.

Another object of the invention is to provide a means of stabilizing urease in a normally denaturing environment.

Still another object of the invention is to provide a means of metering stabilized urease at a rate sufficient to support a digestive reation on a coating having the general structural formula $[N(R)_x]_y$ M.S.

Yet another object of the invention is to provide compositions and a method suitable for reducing the malodor of a public urinal from noxious to slightly noticeable in a matter of a few weeks and subsequently maintaining said urinal at an odor level ranging from slightly noticeable to unpleasant.

These and other objects of the invention will be apparent from the following description of the invention and from the appended drawings which include:

DESCRIPTION OF THE DRAWINGS

FIG. 1 which is a plot of subjective odor level observations, at various times, of urinals treated with the composition of the invention and urinals treated with conventional masking agents; and FIG. 2 which is a plot of the subjective odor level observations and urease/coating reaction products, obtained at various times with various urinals treated with the compositions of the invention and with various untreated urinals.

Description of the Preferred Embodiment

It has been found that the odor characteristic of public urinals can be reduced dramatically and generally controlled to such an extent that the various odor masking products traditionally used are no longer necessary and the odor is reduced to an acceptable level.

The source of the odor problem is now thought to be that portion of the urinal discharge system which allows some of the urine and the water used in flushing to collect and form a coating on the discharge system substrate. This coating can generally be described as an insoluble precipitate which deposits at a rate dependent on the use of the urinal and the rate of flow of the flushing water.

It is believed that the coating thus formed reacts continuously with bacteria present in this environment to produce the various offensive odors generally identified with public rest rooms. Thus, it can be appreciated that this odor problem is thought to be directly related to the formation of the insoluble coatings in the urinal discharge system.

Most urinal discharge systems are characterized by a series of depressions and sites where a water/urine mixture collects. These depressions are generally located near the base of the urinal. These depressions could be described as collection sites and are generally characterized by their proximity to the base of the urinal and their ready access to air and bacteria which are thought to play a key role in the formation of malodors.

The odor causing coatings which form in the collection sites or urinal discharge systems can be described generally by the following structural formula:

$[N(R)_x]_y$ M.S. wherein:

N is nitrogen,

R is hydrogen and/or organo moieties such as alkyl carboxyl, carbonyl and mixtures thereof, M is a metal generally found in hard water such as Fe, Ca, Mg, Mn, Sn, Al, Pb, Cu, Cr, Na, and mixtures thereof, S is a salt or salts generally found in hard water including phosphates, sulfates, chlorides, bromides, chlorates, silicates, permanganates and mixtures thereof, and $x$ and $y$ are whole numbers from 1 to 4.

It is thought that once this insoluble coating forms it continues to build up and to react with bacteria in the presence of water, sluffs off various odor forming substances which can generally be represented by the formulas $N(R)_{x'}$ $[N(R)_x]_y S$ where N,R,S, and x and y are as defined above. This buildup and sluffing off is thought to approach a state of equilibrium and is considered to be the continuing source of noxious odors characteristic of these systems.

It has been found that if this insoluble coating is periodically flushed with water which has been modified by passing it over a solid isotropic composition comprising a controlled release agent and stabilized urease, that the coating is modified to such an extent by the water/controlled release agent/stabilized urease that the odor problem characteristic of the coating is reduced significantly and the need to use conventional masking agents is generally reduced and oftentimes avoided altogether. It has been observed that once the collection sites have been subjected to a continuous and prolonged treatment with from 200,000 to 400,000 Sumner Units of stabilized urease over 8 weeks that the odors given off at these sites are substantially reduced. Thereafter, it has been found that a periodic flushing of the collection sites with a reduced level of stabilized urease, i.e. 100,000 to 200,000 Sumner Units per 8 weeks, is sufficient to maintain the urinal at a substantially reduced malodor level.

It is apparent that the stabilized urease reacts with the metal salts in the substrate to form a soluble material that is flushed away without the odor characteristic of the sluffing which occurs with untreated urinals. These observations are further illustrated in FIGS. 1 and 2.

For the purpose of the present invention, the activity of Urease will be described in Sumner Units. A Sumner Unit (SU) of urease activity is that amount of urease which will liberate one milligram of ammonia nitrogen from a urea-phosphate solution buffered at pH 7.0 in five minutes and at 20° C. (See Sumner, J.B., and Graham, V.A., Proc. Soc. Exp—1 Biol. Med. 22,504 (1925).

The composition of the invention is a solid, isotropic composition comprising controlled release agent and stabilized urease. The controlled release agent is comprised of a granular block having a solubilization density from about 15 to 90 grams/per week and contains up to 99.9% by weight of a solubilized salt. This salt can be organic, or inorganic and includes paradichlorobenzene, sodium hexametaphosphate, sodium benzoate, sodium sulphate, calcium aluminum silicate, trisodium pyrophosphate, sodium tripolyphosphate and mixtures of these salts. In a preferred embodiment, the salt has subliming properties such as paradichlorobenzene.

The solubilization density of the composition is defined as the weight in grams of the composition that is solubilized under standard conditions of water flow and temperature. The physical properties of the salt, the compression pressures used to form the isotropic block and the use of solubilization additives aid in controlling the solubilization density of the composition of the invention. The solubilization density of the compositions of the invention is obtained by measuring the amount of the composition formed in the shape of a round block 3 inches in diameter and ½ inch thick which is dissolved under standard conditions of ambient temperature, and a flow of about one gallon per hour of tap water at about ambient conditions. The average solubilization density of compositions of the invention is found to range from between about 20 grams/per week to about 90 grams/per week. In a preferred embodiment the solubilization density is from about 30 to 70 grams/per week. In a particularly preferred embodiment the solubilization density is between about 40 and 50 grams/per week.

The salts suitable for use as a controlled release agent are mixed with the stabilized urease under conditions suitable for producing a uniform, isotropic mixture of the urease throughout the controlled release agent block. Generally, the salts used as the controlled release agent have a melting temperature below about 145° C and preferably below about 100° C. When forming the isotropic mixtures of the invention, the salts are melted and the stabilized urease is added to the salt prior to crystallization. The selection of salts can be expanded further by employing various surfactants which function as melting control agents. Examples of these surface active materials include, sodium lauryl sulfate, sodium sarcosinate and the like.

The salt/urease mixture is then allowed to cool. During the manufacturing process, if the salt melts and can be formed into a solid block, it is suitable for the invention without further processing. However, if the salt used does not melt, the salt crystals are mixed with an appropriate concentration of urease and compressed with a standard industrial block forming device under pressures ranging from 2 to 100 tons per square inch. The solid blocks produced in either manner are characterized by:

a. An isotropic mixture of the urease and the salt with a solubilization activity between about 500 and about 4000 SU per gram of controlled release agent, and b. An average solubilization density from between about 20 to about 90 grams per week.

In a preferred embodiment of the invention optimum urease stability is obtained if the controlled release agent is substantially free from water of hydration.

For the purpose of the invention, the solubilization activity of the composition of the invention is defined as the amount of active urease in SU released by the composition per gram of total composition solubilized under the conditions described above for defining the average solubilization density.

It has been observed that, the solubilization activity is not only a function of the concentration of urease dispersed uniformly throughout the controlled release agent, but is also a function of the stability of the urease; the rate of solution of the controlled release agent and the concentration of water in the isotropic mixture. It has been found that the compositions of the invention are particularly effective on critical odor forming coatings if the solubilization activity is above about 2000 SU of urease per gram of the solid isotropic composition and preferably between about 2000 and about 4000 SU of urease per gram of solid isotropic composition. Once the odor causing coating has been treated with the composition of the invention, or if the malodor condition is not acute, it has been found that the solubilization activity can be reduced to an activity in the range from about 500 to about 2000 SU of urease/per gram of solid isotropic composition.

It is well established that urease is very soluble in water, and in certain aqueous media such as solutions containing metal ions urease is most susceptible to denaturation. An unexpected and unobvious advantage of the composition of the present invention is that the composition containing stabilized urease retains its solubilization activity at the dilution levels used and in the presence of the metal ions generally found in hard water. Specifically, metal ions such as iron, copper, and lead have been reported to be particularly effective in denaturing urease even when these metal ions are present in trace amounts. Surprisingly, after weeks of exposure to intermittent washing with hard water it was observed that the urease released by the controlled release agent of the invention was still active at the urinal collection sites.

THE METHOD

In a preferred method of treating urinals, each of the urinals in a public rest room are treated initially with:

a. One 3 ounce block of the composition of the invention; wherein the composition has a solubilization activity between about 2000 and about 4000 SU per gram of solid isotropic composition and wherein the composition has a solubilization density of between about 50 and about 90 grams/per week, followed by b. a succession of three ounce blocks of the composition of the invention having a solubilization activity between about 500 and about 2000 SU per gram of solid isotropic compositions and a solubilization density between 15 and about 25 gram/per week.

The initial block has been found to last approximately one week and produce the most significant change in the odor causing coating. Each of the subsequent blocks have been observed to last for approximately four weeks and provide a lower level of continuous release of the urease sufficient to maintain the urinal at an acceptable level of odor discharge. In these observations, the odor blocks traditionally used as masking agents were not used. After about 10 to 14 weeks of treatment, the odor in the rest room was reduced. These observations are further illustrated in FIG. 1.

The block comprising the controlled release agent/stabilized urease mixture is isotropic and therefore, the stabilized urease does not leach out of the controlled release agent when exposed to water under conditions suitable for solubilization. Rather, only as the controlled release agent dissolves is the stabilized urease released. Thus, the solubilization activity and solubilization density define functions which in combination are critical to the malodor control properties of the compositions of the invention. In addition, the block also functions as a visual indicator that the coating on the urinal substrate is undergoing treatment. For example, when the last of the block dissolves and disappears, this is a signal that the coating is no longer being treated and a new block should be placed in the urinal to continue the malodor control.

The compositions of the invention are found to release the stabilized urease at an accelerated rate when the composition is exposed to water at a higher temperature. Surprisingly, the activity of the stabilized urease is not significantly effected by such higher water temperature conditions.

The stability of the urease is critical to the performance of the composition of the invention. That is, if the urease is not stabilized, it will be ineffective upon release from the composition of the invention. Or if the urease is subject to denaturing it will not be suitable for reacting with the coating to reduce the malodor condition. It has been discovered that purified urease which has an activity of about 150,000 SU per gram and/or urease obtained by means of microbial production can only be used if steps are taken to stabilize the enzyme. For example, these purified forms of urease can be coated or encapsulated or the enzyme can be immobilized by incorporating it on a substrate such as glass or resin.

It has been found that urease derived from the jack bean in its unpurified, unextracted form is particularly suited for processing with the salts which comprise the controlled release agent and for reacting with the coating of the urinal discharge substrate. Unexpectedly the activity of the jack bean derived urease does not change significantly during storage nor during solubilization of the composition as is apparent from the solubilization activity of the compositions of the invention. If the urease were not stable, the solubilization activity of the composition of the invention would decrease substantially as the block dissolves during solubilization. That this does not occur with the compositions of the invention is shown by FIGS. 1 and 2. It is suggested that perhaps some of the critical mercapto groups of the urease molecule which are responsible for its enzymatic activity are screened from the denaturing influences of the metal ions and the like by some of the impurities present in the jack bean.

In a preferred embodiment, the stabilized urease is mixed with an accelerator such as cellulase, hemicellulase, protease and mixtures of these materials. This accelerator is generally preferred in a concentration from between about 1000 to about 5000 Delft units of protease per gram and 100 to 600 CMC units of cellulase per gram of the composition. However, concentrations from between about 1000 to about 10,000 Delft units of protease and 100 to 3000 CMC units of cellulase per gram of the composition have been found useful. The accelerators are thought to react with the stabilized urease making it available for reaction at the collection sites.

Additional materials can be used in the compositions of the invention provided they do not effect adversely the critical properties of the composition. For example, dyes, fragrances and solubilization control agents such as petroleum derivatives like wax and resins can be used. Additionally, the blocks of controlled release agents and stabilized urease are preferably packaged with various film forming materials such as paper, foil, polyethylene, polypropylene, saran, cellophane and the like.

The following examples further illustrate the compositions of the invention:

Example 1 – 95 pounds of commercial grade paradichlorobenzene was mixed with 5 pounds of jack bean derived urease having an activity of 4000 SU per gram. To this mixture ¼ pound of cellulase, ¼ pound of protease and 1/10 pound of dye were added. This mixture was mixed with a blender for about 15 minutes at ambient conditions. The resultant mixture was then weighed out into three ounce portions and pressed approximately .5 inches thick. Each of the blocks were wrapped with a cellophane sheet. After storage under ambient conditions for six months, the blocks were found to have a urease activity of approximately 3600 SU per gram. The solubilization activity of the block was determined by exposing the block to air and an intermittent flow of tap water at ambient temperature at the rate of approximately 1 gal. per hour. The stabilized urease activity was determined using the standard activity procedures and readings were made when the block weighed 2.5 ounces, 2 ounces, 1.5 ounces, 1 ounce and 0.5 ounces. The urease activity did not change significantly and remained between about 500 and about 4000 SU per gram. The solubilization density was found to range from between about 20 grams per week to about 90 grams per week.

When the blocks of this composition were placed at the discharge port of each of several urinals in a public urinal system, they were observed to last approximately 4 weeks. At the end of each 4 week period a new block was added to each urinal. The odor of the urinal was evaluated daily and recorded. When the results obtained with this composition were compared with the observations obtained with similar urinals treated with only a conventional masking agent, the advantages of the composition are apparent. These comparative results are illustrated in FIGS. 1 and 2.

The following are illustrative examples showing various alternative embodiments of this invention. It is understood that these examples are merely illustrative of suitable compositions of the invention and are not to be construed as limiting the scope of the invention.

| Example | 2 | 3 | 4 | 5 | 6 | 7 | 8 |
|---|---|---|---|---|---|---|---|
| Controlled release agent salt | paradichloro benezene | sodium hexameta phosphate | sodium benzoate | sodium sulphate | calcium aluminum silicate | trisodium pyrophosphate | sodium tripolyphosphate |
| % by wght. salt | 95 | 99.9 | 80 | 50 paradichloro benzene 45 | 60 sodium tri- polyphosphate 36.9 | 15 paradichloro benezene 75 | 96 |
| Solubilization density - gm/per week | 20 | 90 | 20 | 45 | 100 | 20 | 30 |
| Tons of pressure to form the block | 15 | 5 | 80 | 20 | 10 | 30 | 60 |
| Solubilization additives (% by wght.) | wax (2%) | none | mixture of wax and resin having an avg. mol. wght. of 5000 (10%) | resin having an avg. mol. wgt. of 2500 (1.1%) | surfactant 1% | surfactant 5% | wax (2%) |
| Type of urease (% by wght.) | jack bean meal (3) | purified extract from jack bean (0.08) | microbial (8) | jack bean meal (2.5) | purified extract from jack bean (.1) | jack bean meal (4) | microbial (2.0) |
| Solubilization activity SU per gram | 750 | 4000 | 500 | 1000 | 1500 | 2000 | 4000 |
| Type of accelerator (% by wght.) | mixture of hemicell- ulase cel- ulase (.5) | mixture of hemicellulase celulase (0.02) | none | mixture of hemicellulase celulase (.3) | | mixture of hemicellulase celulase (.5) | none |
| Other additives (% by wght.) | protease (.4) dye (.1) | Na₂EDTA (1.0) | protease (1) | protease (1) Na₂EDTA (1.0) amylase (.1) | dye (.1) fragrance (.1) protease (1.8) | dye (.1) fragrance (.2) protease (.2) | none |
| | | | dye (.5) fragrance (.5) | | | | |
| % water of hydration | — | 5 | 10 | 15 | 10 | | — |
| Type of wrapping | cellophane | foil | saran | polyethylene | paper | foil | B polypropylene |

It has been observed that certain chelating agents such as sodium ethylenediamine tetraacetic acid increase the yield of ammonia under the conditions used with the present invention. Such increases are unexpected and improve the performance of the composition of the invention. Additionally excess chelating agents function to complex some of the metal ions present.

It is understood that the composition illustrated in the above examples may be modified as will become apparent to those skilled in the art, without departing from the scope of the invention as defined in the appended claims.

What is claimed is:

1. A composition of matter comprising:
   a. a solid, isotropic, controlled release agent,
   b. stabilized urease, and
   c. an accelerator, said accelerator being an enzyme selected from the group consisting of cellulase, hemi-cellulase, protease, and mixtures thereof.

2. A composition of matter according to claim 1 wherein the composition has a solubilization activity from between about 500 and about 4000 Sumner Units per gram.

3. A composition of matter according to claim 1 wherein the urease is derived from the jack bean.

4. A composition of matter according to claim 1 wherein the release agent comprises a material selected from the group consisting of paradichlorobenzene, sodium hexametaphosphate, sodium benzoate, sodium sulphate, calcium aluminum silicate, trisodium pyrophosphate, sodium tripolyphosphate and mixtures thereof.

5. A composition of matter according to claim 1 wherein the composition is substantially free from water of hydration.

6. A composition of matter according to claim 1 wherein the release agent comprises a material having a melting temperature below about 145° C.

7. A solid isotropic composition of matter containing:
   a. a controlled release agent containing up to about 99.9% by weight of a material having a melting point below about 145° C., and selected from the group consisting of paradichlorobenzene, sodium hexametaphosphate, sodium benzoate, sodium sulphate, calcium aluminum silicate, trisodium pyrophosphate, sodium tripolyphosphate and mixtures thereof, and
   b. stabilized urease, wherein the composition has a solubilization activity from between about 500 and about 4000 Sumner Units per gram and a solubilization density from between about 15 and about 90 grams/per week.

8. A composition according to claim 7 wherein the controlled release agent contains a melting point control agent.

9. The composition of claim 8, wherein the melting point control agent is selected from the group consisting of sodium lauryl sulfate, sodium sarcosinate, and mixtures thereof.

10. A composition according to claim 7 containing up to about 2 percent by weight of an accelerator having an activity from between about 1000 and about 10,000 Delft units per gram and selected from the group consisting of cellulase, hemicellulase, protease, and mixtures thereof.

11. A method of treating a urinal discharge system having an odor causing coating, comprising exposing the coating to a solid isotropic composition containing a controlled release agent and stabilized urease in the presence of water at a rate and for a period of time sufficient to support a continuous digestive reaction of stabilized urease with the coating.

12. A method of treating a urinal discharge system according to claim 11 wherein the coating is treated with:
   a. a first composition having a solubilization activity between about 2000 and about 4000 Sumner Units per gram of controlled release agent and a solubilization density between about 50 and about 90 grams/per week, and subsequently
   b. a second composition having a solubilization activity between about 500 and about 2000 Sumner Units per gram of controlled release agent and a solubilization density between about 15 and about 25 grams/per week.

13. A process for producing a solid, isotropic composition containing a controlled release agent and stabilized urease comprising:
   a. melting a substance selected from the group consisting of paradichlorobenzene, sodium hexametaphosphate, sodium benzoate, sodium sulphate, calcium aluminum silicate, trisodium pyrophosphate, sodium tripolyphosphate and mixtures thereof, said substance having a melting temperature below about 145° C.,
   b. blending jack bean derived urease into the melted substance prior to crystallization, and
   c. compressing the urease/substance mixture under a pressure from about 2 to about 100 tons/sq. inch to provide a solid mass having an average solubilization density from between about 15 to about 90 grams/per week and a urease solubilization activity from between about 500 to about 4000 Sumner Units per gram.

14. A method of controlling odors, comprising placing a solid isotropic composition of matter in a urinal, said composition comprising:
   a. a solid, isotropic controlled release agent containing up to 99.9% by weight of a material selected from the group consisting of paradichlorobenzene, sodium hexametaphosphate, sodium benzoate, trisodium pyrophosphate, sodium sulfate, calcium aluminum silicate, sodium triployphosphate, and mixtures thereof, and
   b. stabilized urease.

* * * * *